United States Patent
Doi et al.

(10) Patent No.: US 8,415,627 B2
(45) Date of Patent: Apr. 9, 2013

(54) FLUORESCENCE DETECTION DEVICE USING INTENSITY-MODULATED LASER LIGHT AND FLUORESCENCE DETECTION METHOD

(75) Inventors: Kyouji Doi, Tamano (JP); Shigeyuki Nakada, Tamano (JP); Hironori Hayashi, Tamano (JP); Kazuteru Hoshishima, Tamano (JM)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 0 days.

(21) Appl. No.: 13/119,696

(22) PCT Filed: Sep. 16, 2009

(86) PCT No.: PCT/JP2009/004644
§ 371 (c)(1),
(2), (4) Date: Mar. 17, 2011

(87) PCT Pub. No.: WO2010/032451
PCT Pub. Date: Mar. 25, 2010

(65) Prior Publication Data
US 2011/0168916 A1   Jul. 14, 2011

(30) Foreign Application Priority Data
Sep. 19, 2008   (JP) ................. 2008-240970

(51) Int. Cl.
*G01J 1/42* (2006.01)
*G01J 1/58* (2006.01)
*G21K 5/00* (2006.01)

(52) U.S. Cl. ............... 250/354.1; 250/458.1; 250/459.1; 250/393

(58) Field of Classification Search ............... 250/459.1, 250/458.1, 214 DC, 354.1, 393, 395; 702/1, 702/22, 24, 25, 27, 28, 30, 32, 127, 187, 702/189
See application file for complete search history.

(56) References Cited

U.S. PATENT DOCUMENTS

| 4,937,457 A | 6/1990 | Mitchell |
| 5,270,548 A | 12/1993 | Steinkamp |
| 5,315,122 A | 5/1994 | Pinsky et al. |

(Continued)

FOREIGN PATENT DOCUMENTS

| EP | 0 259 973 A2 | 3/1988 |
| EP | 1 746 411 A1 | 1/2007 |

(Continued)

OTHER PUBLICATIONS

Extended European Search Report of the corresponding European Application No. 09814296.1, dated Mar. 5, 2012.

(Continued)

*Primary Examiner* — David Porta
*Assistant Examiner* — Abra Fein
(74) *Attorney, Agent, or Firm* — Global IP Counselors, LLP

(57) ABSTRACT

Fluorescence detection device employed in a flow site meter emits laser light intensity-modulated by a modulation signal and acquires the fluorescence signal of fluorescence emitted from a measurement object passing through a measurement point of the laser light. The device generates the reference signal, separately from the modulation signal, the reference signal having a frequency different from the frequency of the modulation signal and having a phase synchronized with a phase of the modulation. The device determines fluorescence relaxation time of the measurement object from the fluorescence signal using the reference signal.

17 Claims, 8 Drawing Sheets

U.S. PATENT DOCUMENTS

| | | | |
|---|---|---|---|
| 5,317,162 A | | 5/1994 | Pinsky et al. |
| 5,504,337 A | * | 4/1996 | Lakowicz et al. .......... 250/461.2 |
| 5,757,013 A | | 5/1998 | Groger et al. |
| 5,990,484 A | * | 11/1999 | Ohsuka ...................... 250/458.1 |
| 6,201,628 B1 | | 3/2001 | Basiji et al. |
| 6,426,505 B1 | | 7/2002 | Rao et al. |
| 7,822,558 B2 | * | 10/2010 | Kimura et al. ................... 702/23 |
| 2007/0030487 A1 | * | 2/2007 | Willing et al. ................. 356/437 |
| 2008/0024779 A1 | * | 1/2008 | Aasmul ......................... 356/317 |
| 2010/0312482 A1 | * | 12/2010 | Nakada et al. ................... 702/19 |
| 2010/0320398 A1 | * | 12/2010 | Hoshishima et al. ...... 250/459.1 |

FOREIGN PATENT DOCUMENTS

| | | |
|---|---|---|
| JP | 2001-523830 A | 11/2001 |
| JP | 2007-240424 A | 9/2007 |
| JP | 2008-508506 A | 3/2008 |
| WO | WO-98/12521 A1 | 3/1998 |
| WO | WO-03/027648 A2 | 4/2003 |

OTHER PUBLICATIONS

John A. Steinkamp et al., "Flow cytometric, time-resolved measurements by frequency heterodyning of fluorescence emission signals", Proceedings of SPIE, Jan. 1, 2001, pp. 166-174, vol. 4260, Bioscience Divisionk, Los Alamos National Laboratory, Los Alamos, NM 87545, USA.

* cited by examiner

FLUORESCENCE DETECTION DEVICE USING INTENSITY-MODULATED LASER LIGHT AND FLUORESCENCE DETECTION METHOD

TECHNICAL FIELD

The present invention relates to a fluorescence detection device and a fluorescence detection method, in which a measurement object is irradiated with intensity-modulated laser light, fluorescence emitted from the measurement object by irradiation with the laser light is received to obtain a fluorescent signal, and the fluorescent signal is processed. More specifically, the present invention relates to a fluorescence detection device and a fluorescence detection method, which are applied to, for example, an analyzer, such as a flow cytometer for use in medical and biological fields, for analyzing measurement objects such as proteins, cells, DNA, or RNA in a short period of time by identifying each of the measurement objects with the use of fluorescence emitted from a fluorochrome.

BACKGROUND ART

A flow cytometer for use in medical and biological fields includes a fluorescence detection device that receives fluorescence emitted from a fluorochrome in a measurement object irradiated with laser light and identifies the type of measurement object. In the field of medicine, research on the interaction between proteins such as biological binding is being actively conducted. Particularly, research on the interaction between proteins using measurement of fluorescence resonance energy transfer (FRET) is being vigorously pursued. FRET is conventionally measured based on a change in fluorescence intensity, but in recent years, various flow cytometers that analyze measurement objects by utilizing a difference in fluorescence relaxation time (fluorescence lifetime) have been proposed.

In a general flow cytometer, a flow cell is formed by allowing a suspension liquid containing measurement objects, such as biological substances (e.g., proteins, cells, DNA, RNA, or enzymes), labeled with fluorochromes (fluorescent reagents) to flow in a sheath liquid flowing under pressure through a tube at a flow rate of 10 m/sec or less. Each of the measurement objects in the flow cell is irradiated with laser light, and fluorescence emitted from a fluorochrome attached to the measurement object is received. Each of the measurement objects is identified by identifying received fluorescence as a label.

Such a flow cytometer can measure, for example, the relative amount of a measurement object, such as DNA, RNA, an enzyme, or a protein, contained in an individual cell and analyze the property of the measurement object in a short period of time. Further, after identifying a specific type of cell or chromosome based on fluorescence, a cell sorter or the like is used to sort only the identified cell or chromosome in the living state in a short period of time. In this case, it is necessary to accurately identify a larger number of measurement objects in a short period of time based on the information of fluorescence.

Patent Document 1 discloses a device and method for identifying individual particles or cells labeled with different fluorochromes based on the lifetime (fluorescence relaxation time) of their fluorescence.

According to the Patent Document 1, laser light whose intensity has been modulated by a modulation signal from a modulator is emitted from a light source toward an irradiation port of a flow chamber to illuminate an individual particle or cell. Fluorescence emitted from an individual particle or cell is converted into a fluorescent signal by a photodetector and sent to two mixers.

On the other hand, the modulation signal from the modulator is sent to the two mixers via a variable phase shifter. At this time, the phase of the modulation signal to be supplied to one of the mixers is shifted by 90 degrees by a 90 degrees phase shifter that shifts the phase of a signal by 90 degrees, and the phase of the modulation signal to be supplied to the other mixer is not shifted and therefore the modulation signal from the modulator is directly sent to the other mixer.

The fluorescent signal and the modulation signal sent to each of the mixers in such a manner as described above are mixed and passed through a low-pass filter to obtain a real part component and an imaginary part component which are information about the phase delay of the fluorescent signal. From the ratio between the real part component and the imaginary part component, fluorescence lifetime is calculated.

The Patent Document 1 describes that individual particles or cells can be identified based on the lifetime of their fluorescence.

In addition to the Patent Document 1, Patent Documents 2 and 3 also each disclose a flow cytometer that identifies individual particles or cells by determining the lifetime of their fluorescence from the phase delay of the fluorescence.

PRIOR ART DOCUMENTS

Patent Documents
Patent Document 1: U.S. Pat. No. 5,504,337
Patent Document 2: U.S. Pat. No. 5,270,548
Patent Document 3: U.S. Pat. No. 5,317,162

However, in such a flow cytometer disclosed in each of the Patent Documents 1 to 3, the real part component (cosine component) and the imaginary part component (sine component), which are information about the phase delay of the fluorescent signal relative to the modulation signal, shall have constant values. On the other hand, the mixer that mixes the fluorescent signal and the modulation signal outputs a mixed signal containing a DC component offset due to the modulation signal. The offset has a significant influence on the information about phase delay for determining the fluorescence relaxation time of fluorescence when the fluorescence intensity of the fluorescent signal is weak (i.e., when the level of the fluorescence signal is low). Therefore, the flow cytometers disclosed in the Patent Documents 1 to 3 have a problem in that they cannot necessarily calculate fluorescence relaxation time accurately.

SUMMARY OF THE INVENTION

Problems to be Solved by the Invention

In order to solve the above problem, it is an object of the present invention to provide a device and method for detecting fluorescence by irradiating a measurement object with laser light whose intensity has been modulated at a predetermined frequency, receiving fluorescence emitted from the measurement object to obtain a fluorescent signal, and processing the fluorescent signal, which are capable of calculating fluorescence relaxation time with a higher degree of accuracy as compared to a conventional case even when a mixed signal outputted by a mixer contains a DC component as in the conventional case.

Means for Solving the Problem

An aspect of the present invention provides a fluorescence detection device using intensity-modulated laser light, which irradiates a measurement object with laser light, receives fluorescence emitted from the measurement object to obtain a fluorescent signal, and determines fluorescence relaxation time from the fluorescent signal. The fluorescence detection device includes:

a laser light source unit emitting intensity-modulated laser light with which a measurement object is to be irradiated;

a light-receiving unit outputting a fluorescent signal of fluorescence emitted from the measurement object irradiated with intensity-modulated laser light;

a signal generating unit generating a modulation signal having a predetermined frequency to modulate an intensity of the laser light emitted from the laser light source unit and generating, separately from the modulation signal, a first reference signal having a frequency different from that of the modulation signal in synchronization with the modulation signal;

a signal processing unit comprising a first mixer that performs first mixing processing to mix the first reference signal and the fluorescent signal outputted from the light-receiving unit by irradiating the measurement object with the laser light whose intensity has been modulated using the modulation signal and a first low-pass filter that performs, on a mixed signal obtained by the first mixing processing, first low-pass filtering using a cut-off frequency lower than a sum frequency of a frequency of the modulation signal and a frequency of the first reference signal but higher than a difference frequency between the frequency of the modulation signal and the frequency of the first reference signal to output a fluorescent signal-based low-frequency signal; and a fluorescence detection unit that converts the fluorescent signal-based low-frequency signal into a digital signal and calculates a phase of the fluorescent signal relative to the modulation signal using a first signal component of the digital signal which corresponds to the difference frequency to determine a fluorescence relaxation time of the fluorescence emitted from the measurement object from the calculated phase.

Preferably, the signal generating unit comprises a first oscillator that generates a clock signal, a second oscillator that generates the modulation signal in synchronization with the clock signal generated by the first oscillator, and a third oscillator that generates the first reference signal in synchronization with the clock signal.

The fluorescence detection unit may mix a second reference signal, which is a digital signal having the difference frequency as a frequency thereof, and the digitized fluorescent signal-based low-frequency signal to determine the first signal component.

The fluorescence detection unit may generate the second reference signal. Alternatively, the signal processing unit may include a second mixer that performs second mixing processing to mix the modulation signal and the first reference signal and a second low-pass filter that performs, on a mixed signal obtained by the second mixing processing, second low-pass filtering using a cut-off frequency lower than the sum frequency but higher than the difference frequency to output a sine-wave signal having the difference frequency as the frequency thereof, and the fluorescence detection unit may digitize the sine-wave signal outputted from the second low-pass filter to generate the second reference signal.

The fluorescence detection unit may perform FFT (Fast Fourier Transformation) processing on the digitized fluorescent signal-based low-frequency signal to calculate, as the first signal component, a value of a real part and a value of an imaginary part, which are obtained by the FFT processing and correspond to the difference frequency, and may calculate the phase from the value of the real part and the value of the imaginary part.

The light-receiving unit may include, in addition to a light-receiving element that receives the fluorescence, a light-receiving element that receives side-scattered light obtained by irradiating the measurement object with the laser light, and outputs a light-receiving signal obtained by receiving the side-scattered light. The signal processing unit may include a third mixer that performs third mixing processing to mix the light-receiving signal and the first reference signal and a third low-pass filter that performs, on a mixed signal obtained by the third mixing processing, third low-pass filtering using a cut-off frequency lower than the sum frequency but higher than the difference frequency to output a light-receiving signal-based low-frequency signal. The fluorescence detection unit may determine a phase of a second signal component of the light-receiving signal-based low-frequency signal, which corresponds to the difference frequency, by mixing the light-receiving signal-based low-frequency signal and the second reference signal or by performing FFT processing on the light-receiving signal-based low-frequency signal, may correct the phase of the fluorescent signal based on the phase of the second signal component, and may determine a fluorescence relaxation time of fluorescence emitted from a measurement object using the corrected phase.

The signal processing unit may include:

a second mixer that performs second mixing processing to mix the modulation signal and the first reference signal and a second low-pass filter that performs, on a mixed signal obtained by the second mixing processing, second low-pass filtering using a cut-off frequency lower than the sum frequency but higher than the difference frequency to output a sine-wave signal having the difference frequency as the frequency thereof.

The fluorescence detection unit may digitize the sine-wave signal outputted from the second low-pass filter to generate the second reference signal, correct the phase of the fluorescent signal by subtracting a phase of the second reference signal from the phase of the fluorescent signal to determine a fluorescence relaxation time of the fluorescence emitted from the measurement object using the corrected phase.

The fluorescence detection unit may determine a phase of the second reference signal by performing FFT processing on the second reference signal or by mixing the second reference signal and a separately-generated sine-wave signal having the difference frequency.

When the fluorescence detection unit mixes the second reference signal and the separately-generated sine-wave signal having the difference signal, a sine signal and a cosine signal may be each mixed with the second reference signal and a ratio between a value obtained by mixing the sine signal with the second reference signal and a value obtained by mixing the cosine signal with the second reference signal may be calculated to determine a phase of the second reference signal.

When the fluorescence relaxation time of the fluorescence emitted from the measurement object is determined, the fluorescence detection unit further may correct the corrected phase of the fluorescent signal using a previously-determined correction amount to determine the fluorescence relaxation time of the fluorescence emitted from the measurement object using the further corrected phase with the correction amount. The correction amount is preferably determined so that when a fluorochrome that emits fluorescence with a known fluorescence relaxation time is set as a measurement object, a fluorescence relaxation time determined by measuring fluorescence becomes equal to the known fluorescence relaxation time of the fluorochrome.

The light-receiving unit may include, in addition to a light-receiving element that receives the fluorescence, a light-receiving element that receives side-scattered light obtained by irradiating the measurement object with the laser light to output a light-receiving signal obtained by receiving the side-scattered light. The signal processing unit may include a third mixer that performs third mixing processing to mix the light-receiving signal and the reference signal and a third low-pass filter that performs, on a mixed signal obtained by the third mixing processing, third low-pass filtering using a cut-off frequency lower than the sum frequency but higher than the difference frequency to output a light-receiving signal-based low-frequency signal having the difference frequency as a frequency thereof. The fluorescence detection unit preferably determines an amplitude of the light-receiving signal-based low-frequency signal. Then, the fluorescence detection unit preferably sets the determined amplitude as an intensity of the side-scattered light and sets an amplitude determined from the first signal component as fluorescence intensity to output the side-scattered light intensity, the fluorescence intensity, and the fluorescence relaxation time.

Another aspect of the invention provides a fluorescence detection method using intensity-modulated laser light, in which fluorescence emitted from a measurement object irradiated with laser light is received and fluorescence relaxation time is determined from a fluorescent signal obtained by receiving the fluorescence. The method includes the steps of:

irradiating a measurement object with laser light whose intensity has been modulated by a modulation signal having a predetermined frequency;

receiving fluorescence emitted from the measurement object irradiated with the laser light by a detection means to acquire a fluorescent signal obtained by the detection means;

generating, separately from the modulation signal, a first reference signal having a frequency different from a frequency of the modulation signal and a phase synchronized with that of the modulation signal;

performing first mixing processing to mix the first reference signal and the fluorescent signal obtained by the detection means by irradiating the measurement object with the intensity-modulated laser light and further performing first low-pass filtering using a cut-off frequency lower than a sum frequency of the frequency of the modulation signal and the frequency of the reference signal but higher than a difference frequency between the frequency of the modulation signal and the frequency of the reference signal to generate a fluorescent signal-based low-frequency signal; and converting the generated fluorescent signal-based low-frequency signal into a digital signal and calculating a phase of the fluorescent signal relative to the modulation signal using a first signal component of the digital signal, the first signal component corresponding to the difference frequency, and determining the fluorescence relaxation time of the fluorescence emitted from the measurement object using the calculated phase.

When a digital sine-wave signal having the difference frequency as a frequency thereof is defined as a second reference signal, the first signal component is preferably determined by mixing the second reference signal and the digitized fluorescent signal-based low-frequency signal.

In addition to the first mixing processing and the first low-pass filtering performed on the fluorescent signal, the second reference signal may be generated by:

performing second mixing processing to mix the modulation signal and the first reference signal, performing, on a mixed signal obtained by the second mixing processing, second low-pass filtering using a cut-off frequency lower than the sum frequency but higher than the difference frequency to output a sine-wave signal having the difference frequency as a frequency thereof and, then digitizing the sine-wave signal obtained by the second low-pass filtering.

When the fluorescence is received, side-scattered light obtained by irradiating the measurement object with the laser light may be received in addition to the fluorescence, and a light-receiving signal obtained by receiving the side-scattered light may be outputted. Then, third mixing processing may be performed to mix the light-receiving signal and the first reference signal and third low-pass filtering using a cut-off frequency lower than the sum frequency but higher than the difference frequency is performed on a mixed signal obtained by the third mixing processing to output a light-receiving signal-based low-frequency signal. A phase of a second signal component of the light-receiving signal-based low-frequency signal, which corresponds to the difference frequency, may be determined by mixing the light-receiving signal-based low-frequency signal and the digital sine-wave signal having the difference frequency as a frequency thereof or by performing FFT processing on the light-receiving signal-based low-frequency signal, and the phase of the fluorescent signal may be corrected based on the phase of the second signal component to determine the fluorescence relaxation time of the fluorescence emitted from the measurement object using the corrected phase.

When the fluorescence relaxation time of the fluorescence emitted from the measurement object is determined from the phase of the fluorescent signal, the phase of the fluorescent signal may be corrected using a previously-determined correction amount and the fluorescence relaxation time of the fluorescence emitted from the measurement object may be determined using the corrected phase. The correction amount is determined so that when a fluorochrome that emits fluorescence with a known fluorescence relaxation time is set as a measurement object to measure fluorescence, the fluorescence relaxation time determined from the corrected phase becomes equal to the known fluorescence relaxation time of the fluorochrome.

Effect of the Invention

In an embodiment of the fluorescence detection device and the fluorescence detection method according to the present invention, the frequency of the modulation signal for modulating the intensity of the laser light and the frequency of the reference signal are set to be different from each other. Accordingly, a signal obtained by low-pass filtering after mixing the reference and the fluorescence signal whose intensity is oscillating at the same frequency as that of the modulation signal, has an AC component including the dominant component of the difference frequency between the frequency of the modulation signal and the frequency of the reference signal. Therefore, the fluorescence relaxation time can be determined by calculating the phase (phase delay) of the fluorescence signal relative to the modulation signal, with higher degree of accuracy than ever before, even when the mixed signal outputted by the mixer includes a DC component offset as before.

The modulation signal and the reference signal are generated by different oscillators. The modulation signal and the reference signal have few noise components generated by the oscillators at the same time. Accordingly a few noise components are included in the signal having the information of the phase delay and obtained by mixing the fluorescence signal and the reference signal. Therefore, the fluorescence relaxation time can be determined with higher degree of accuracy than the conventional art where a single oscillator generates the modulation signal and the reference signal.

In an embodiment of the fluorescence detection device and the fluorescence detection method according to the present invention, the phase of the fluorescence signal is corrected by using information of the phase of the side-scattered light, to remove transmission delay time and signal processing delay time. Alternatively, the phase of the fluorescence signal is corrected by using information of the phase of the signal having, as a frequency thereof, the difference frequency between the frequencies of the modulation signal and the reference signal. Thereby, the phase of the fluorescence signal can be calculated accurately, which makes the fluorescence relaxation time determined with higher degree of accuracy.

In an embodiment of the fluorescence detection device and the fluorescence detection method according to the present invention, the fluorochrome whose fluorescence is emitted with a known fluorescence relaxation time is used as a measurement object. When the fluorescence emitted from the fluorochrome is measured, the fluorescence relaxation time is calibrated with the correction amount for correcting so that the fluorescence relaxation time calculated from the phase of the fluorescence signal may be identical with the known fluorescence relaxation time of the fluorochrome. Accordingly, the fluorescence relaxation time can be determined accurately.

BEST MODE FOR CARRYING OUT THE INVENTION

Hereinbelow, the present invention will be described in detail based on a flow cytometer which suitably employs a fluorescence detection device according to the present invention using intensity-modulated laser light.

Figure 1:
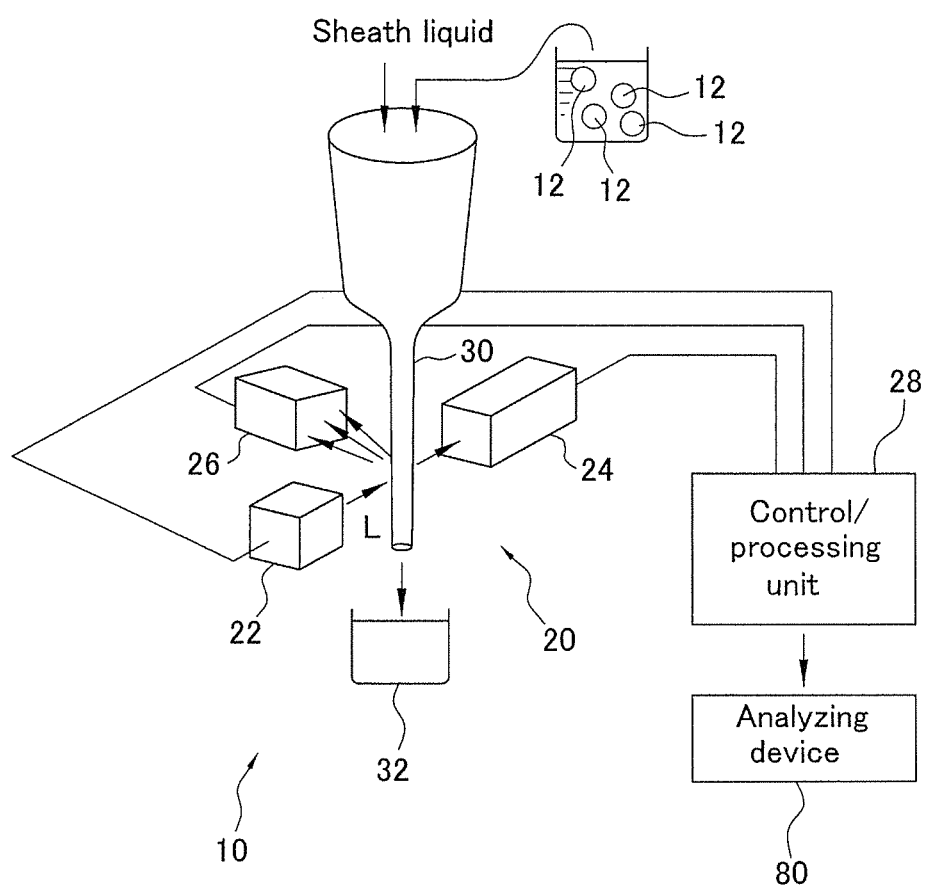
FIG. 1 is a schematic diagram illustrating the structure of a flow cytometer using a fluorescence detection device according to the present invention using intensity-modulated laser light.
Figure 2:
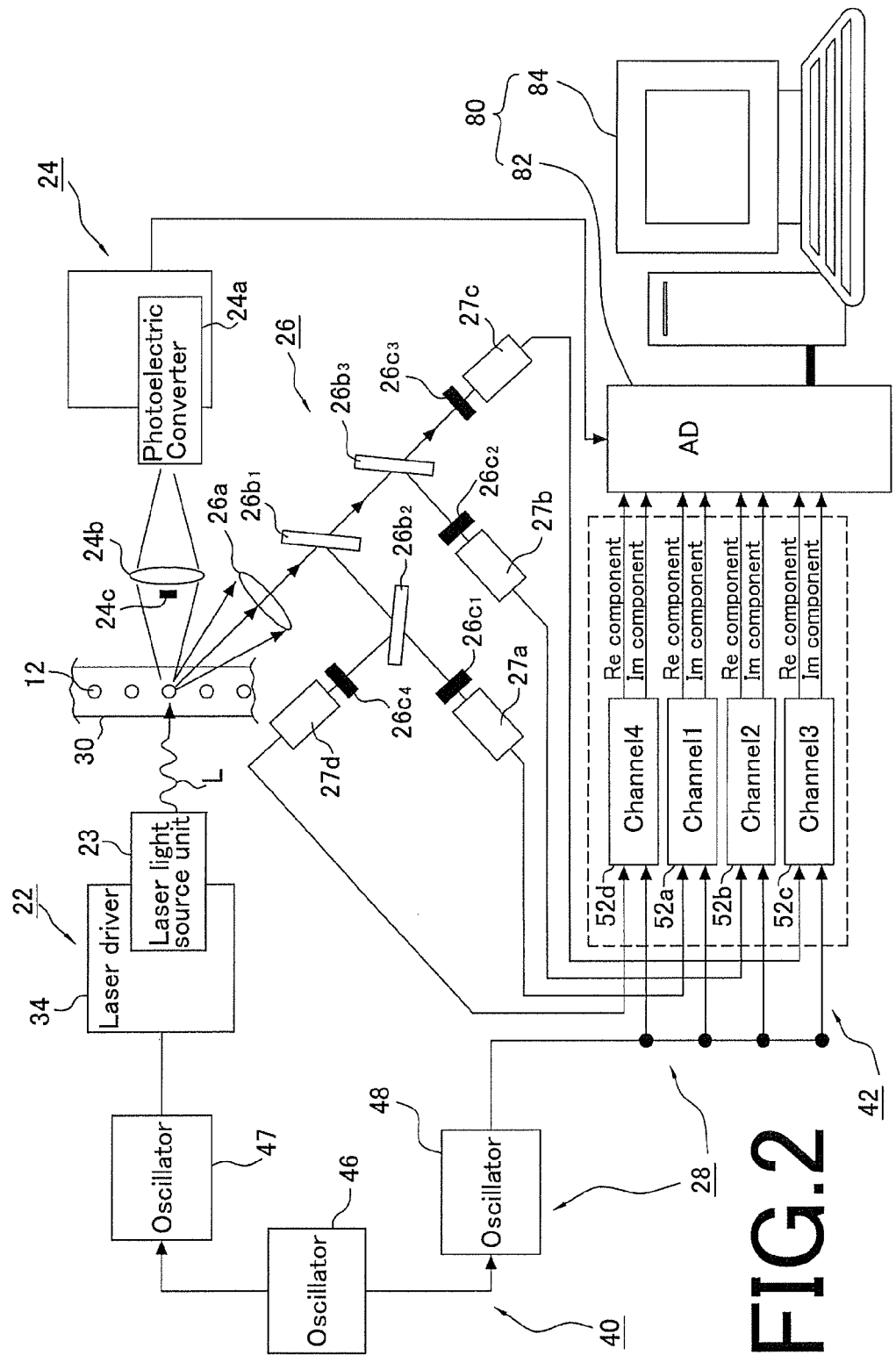
FIG. 2 is a diagram illustrating the structure of the flow cytometer illustrated in FIG. 1 in more detail.

FIG. 1 is a schematic diagram illustrating the structure of a flow cytometer 10 which employs a fluorescence detection device using intensity-modulated laser light L. FIG. 2 is a diagram illustrating the structure of the flow cytometer 10 in more detail. The structure of the flow cytometer 10 will be described below.

The flow cytometer 10 includes a signal processing device 20 and an analyzing device 80. The signal processing device 20 irradiates, with laser light, samples 12, such as proteins to be measured, as measurement objects flowing in line through a flow cell. At this time, the signal processing device 20 detects, as a fluorescent signal, fluorescence emitted from a fluorochrome labeling the sample 12 and processes the fluorescent signal.

The analyzing device 80 determines the fluorescence relaxation time of fluorescence from processing results obtained by the signal processing device 20, and further analyzes a measurement object in the sample 12. That is, the analyzing device 80 corresponds to a fluorescence detection unit of the fluorescence detection device according to the present invention.

The signal processing device 20 includes a laser emitting unit 22, light-receiving units 24 and 26, a control/processing unit 28, and a tube 30. The control/processing unit 28 includes a control unit that modulates the intensity of laser light emitted from the laser emitting unit 22 at a predetermined frequency and a signal processing unit that identifies a fluorescent signal from the sample 12. The tube 30 allows the samples 12 to flow in line in a sheath liquid forming a high-speed flow so as to form a flow cell.

As illustrated in FIG. 1, a collection vessel 32 is provided at the outlet of the tube 30. The flow cytometer 10 may be configured to have a cell sorter for separating a biological substance, such as a specific cell, in the sample 12 in a short period of time after irradiation with laser light L to sort the samples 12 into different collection vessels.

Each of the samples 12 is a measurement object such as a biological substance (e.g., a protein, a cell, DNA, RNA, or an enzyme) and is previously labeled with a fluorescent reagent (fluorochrome), and as illustrated in FIG. 1, a suspension liquid containing the samples 12 is prepared. The samples 12 contain, for example, two or more different kinds of biological substances. In this case, the two or more different kinds of biological substances are labeled with different known pigments, which emit fluorescence of different known wavelengths, as fluorochromes. This makes it possible for the flow cytometer 10 to determine characteristics such as biological binding between the two or more kinds of biological substances.

The samples 12 are not limited to biological substances, and may be, for example, microbeads, each having an artificial structure capable of binding to a specific biological substance.

The laser emitting unit 22 includes a laser light source unit 23 and a laser driver 34.

The laser light source unit 23 is a unit that emits laser light L having a predetermined wavelength. The laser light L is focused on a predetermined position in the tube 30 by a lens system (not illustrated), and the focus position is defined as a measurement point where the sample 12 is measured. The beam diameter of the laser light L at the measurement point is several tens of micrometers. It is to be noted that the laser light source unit 23 emits laser light L having a single wavelength, but may be configured to emit a single beam of laser light combined of two or more beams of laser light. In this case, the laser light source unit 23 uses, for example, a half mirror to combine two or more beams of laser light into a single beam.

The laser light source unit 23 modulates, at a predetermined frequency, the intensity of CW (continuous wave) laser light L of constant intensity and emits intensity-modulated laser light L.

As a light source that emits laser light L, for example, a semiconductor laser is employed.

The laser light L has an output of, for example, about 5 to 100 mW. On the other hand, the frequency (modulating frequency) at which the intensity of laser light L is modulated is, for example, 10 to 50 MHz, whose corresponding time period in a cycle is slightly longer than fluorescence relaxation time.

The laser driver 34 is connected to the control/processing unit 28 to control the output intensity of laser light L. Here, as will be described later, the intensity of each laser light L is modulated at a predetermined frequency in response to a modulation signal.

The laser light source unit 23 emits laser light in a predetermined wavelength band so that laser light L can excite a fluorochrome to allow the fluorochrome to emit fluorescence within a specific wavelength band. The fluorochrome excited by laser light L is attached to the sample 12 such as a biological substance, and therefore when passing through the tube 30 as a measurement object, the sample 12 emits fluorescence at a specific wavelength by irradiation with laser light L at the measurement point.

The light-receiving unit 24 is arranged so as to be opposed to the laser light source unit 23 with the tube 30 being provided therebetween. The light-receiving unit 24 includes a photoelectric converter 24a, a collecting lens 24b, and a blocking plate 24c. The photoelectric converter 24a detects forward-scattered laser light caused by the sample 12 passing through the measurement point and outputs a detection signal indicating the passage of the sample 12 through the measurement point. The blocking plate 24c is used to block the light flux of laser light L so that the photoelectric converter 24a can receive forward-scattered light without directly receiving the light flux of the laser light L.

The signal outputted from the light-receiving unit 24 is used as a trigger signal that informs an AD conversion board 82 (which will be described later) included in the analyzing device 80 on the timing of start of AD conversion and the timing of start of analysis by an analyzing device main body 84 (which will be described later).

On the other hand, the light-receiving unit 26 is arranged, in relation to the measurement point, in a direction orthogonal to both a direction in which laser light emitted from the laser light source unit 23 travels and a direction in which the samples 12 move in the tube 30. The light-receiving unit 26 includes photoelectric converters that receive fluorescence emitted from the sample 12 irradiated with laser light at the measurement point and side-scattered light of the laser light.

FIG. 2 schematically illustrates the structure of an example of the light-receiving unit 26.

The light-receiving unit 26 includes a lens system 26a that focuses a fluorescent signal from the sample 12, dichroic mirrors $26b_1$, $26b_2$, and $26b_3$, band-pass filters $26c_1$, $26c_2$, $26c_3$, and $26c_4$, and photoelectric converters 27a to 27d such as photomultipliers.

The lens system 26a focuses fluorescence incident on the light-receiving unit 26 on the light-receiving surfaces of the photoelectric converters 27a to 27d.

Each of the dichroic mirrors $26b_1$, $26b_2$, and $26b_3$ is a mirror that reflects fluorescence within a predetermined wavelength band but transmits fluorescence without the predetermined wavelength band.

The reflection wavelength bands and transmission wavelength bands of the dichroic mirrors $26b_1$, $26b_2$, and $26b_3$ and the band-pass filters $26c_1$, $26c_2$, $26c_3$, and $26c_4$ are set based on the wavelengths of fluorescence emitted from the sample 12 so that fluorescence within predetermined wavelength bands can pass through the dichroic mirrors $26b_1$, $26b_2$, and $26b_3$ and the band-pass filters $26c_1$, $26c_2$, $26c_3$, and $26c_4$. The dichroic mirror $26b_2$ is a mirror that reflects light within the wavelength range of side-scattered light of laser light but transmits light within a wavelength range including the wavelength of fluorescence.

Each of the band-pass filters $26c_1$, $26c_2$, $26c_3$, and $26c_4$ is a filter that transmits only fluorescence within a predetenmined wavelength band. The band-pass filters $26c_1$, $26c_2$, $26c_3$, and $26c_4$ are provided in front of the photoelectric converters 27a, 27b, 27c, and 27d, respectively. The dichroic mirror $26b_2$ is provided in front of the light-receiving surfaces of the converters 27a and 27d, and the photoelectric converter 27a receives light that has passed through the dichroic mirror $26b_2$, and the photoelectric converter 27d receives light that has been reflected by the dichroic mirror $26b_2$.

The transmission wavelength bands of the band-pass filters $26c_1$, $26c_2$, and $26c_3$ are set so as to correspond to the wavelength bands of fluorescence emitted from fluorochromes, respectively.

Each of the photoelectric converters 27a to 27d including a sensor element equipped with, for example, a photoelectric multiplier is a sensor device that converts light received by its photoelectric surface as a light-receiving surface into an electric signal. Each of the photoelectric converters 27a to 27c receives fluorescence having a predetermined wavelength because the wavelength range of light to be received by each of the photoelectric converters 27a to 27c is limited by the dichroic mirror and the band-pass filter. The photoelectric converter 27d receives side-scattered light of laser light L because the wavelength range of light to be received by the photoelectric converter 27d is limited by the dichroic mirror $26b_2$. In this way, the light-receiving unit 26 receives fluorescence of three different wavelengths and side-scattered light of laser light L.

Here, the fluorescence and the side-scattered light are received by the light-receiving unit 26 as optical signals having signal information that has been subjected to intensity modulation at a given frequency, and therefore signals having a frequency corresponding to the frequency of intensity-modulated laser light L are outputted as fluorescent signals and a light-receiving signal. These fluorescent signals and light-receiving signal are supplied to the control/processing unit 28. Hereinafter, a signal obtained by receiving fluorescence is referred to as a fluorescent signal and a signal obtained by receiving side-scattered light of laser light L is referred to as a light-receiving signal.

The control/processing unit 28 is configured to have a signal generating unit 40 and a signal processing unit 42.

The signal generating unit 40 is a unit that generates a modulation signal for modulating the intensity of laser light at a predetermined frequency (intensity modulation) and a reference signal.

More specifically, the signal generating unit 40 includes an oscillator (first oscillator) 46, an oscillator (second oscillator) 47, and an oscillator (third oscillator) 48. Each of these oscillators may be formed in a circuit.

The oscillator 46 is a clock generator that generates a clock signal having a predetermined frequency.

The oscillator 47 generates a modulation signal for modulating the intensity of laser light L. The modulation signal is allowed to have a single frequency component by a filter (not illustrated), and is supplied to the laser driver 34 via an amplifier. In the laser driver 34, a separately-prepared direct current is superimposed on the modulation signal and supplied to the laser light source unit 23.

As will be described later, the oscillator 48 generates a reference signal (first reference signal) for use in determining fluorescence relaxation time. The modulation signal generated by the oscillator 47 and the reference signal generated by the oscillator 48 are different in frequency, but are in synchronization with each other. The "in synchronization with each other" means that signals are generated with the same phase at the same point of start of signal generation. Therefore, the phases of both the signals periodically become 0 at the same time. The oscillators 47 and 48 each generate a signal in synchronization with the clock signal generated by the oscillator 46. Thus, the modulation signal and the reference signal are generated in synchronization with each other.

A difference frequency between the modulation signal and the reference signal is, for example, 100 kHz or more but 1 MHz or less, and is usually hundreds of kHz. The lower limit of range of the difference frequency is preferably four times the value of 1/T as determined when the time that the sample 12 takes to pass through the measurement point is defined as T (second) and the upper limit of range of the difference frequency is preferably a sampling frequency of the AD conversion board 82 which will be described later.

The signal generating unit 40 may employ, instead of each of the oscillators 47 and 48, a PLL circuit (Phase Locked Loop) equipped with a phase comparator, a loop filter, a voltage control oscillating circuit, and a frequency divider. In this case, the PLL circuits can also generate a modulation signal and a reference signal in synchronization with each other.

The reason why the modulation signal and the reference signal are generated separately from each other in such a manner as described above is that, as compared to a case where one oscillator generates a modulation signal and a reference signal, a mixed signal obtained by mixing the modulation signal and the reference signal by an RF mixer (which will be described later) is less likely to be affected by an oscillator-derived noise component. Further, the modulation signal and the reference signal are generated by different oscillators, and therefore it is possible to reduce the chance that the modulation signal and the reference signal, which are to be mixed together, contain a noise component at the same time.

The reason why the frequencies of the oscillators 47 and 48 are set so that the modulation signal and the reference signal are different in frequency from each other is, as will be described later, to solve the problem accompanying the conventional art, that is, to reduce the influence of a DC component offset contained in a mixed signal obtained by mixing the fluorescent signal and the reference signal by an RF mixer. This point will be described later.

The signal processing unit 42 is a unit that extracts information about the phase of fluorescence emitted from the sample 12 by irradiation with laser light relative to the modulation signal, more specifically, the phase delay of the fluorescence relative to the modulation signal with the use of the fluorescent signals and the light-receiving signal derived from side-scattered light outputted from the photoelectric converters 27a to 27d. More specifically, the signal processing unit 42 includes signal processing channels 1, 2, and 3 that process the fluorescent signals outputted from the photoelectric converters 27a to 27c, respectively, and a signal processing channel 4 that processes the light-receiving signal outputted from the photoelectric converter 27d. The contents of signal processing are the same in all the signal processing channels 1 to 4.

It is to be noted that the above-mentioned information about phase delay includes, for example, a real part component (Re component) and an imaginary part component (Im component) as obtained when the phase delay of a sine-wave signal is represented by a complex number.

The signal processing channel 1 of the signal processing unit 42 includes a processing circuit 52a. The signal processing channels 2 to 4 include processing circuits 52b to 52d, respectively.

Figure 3:
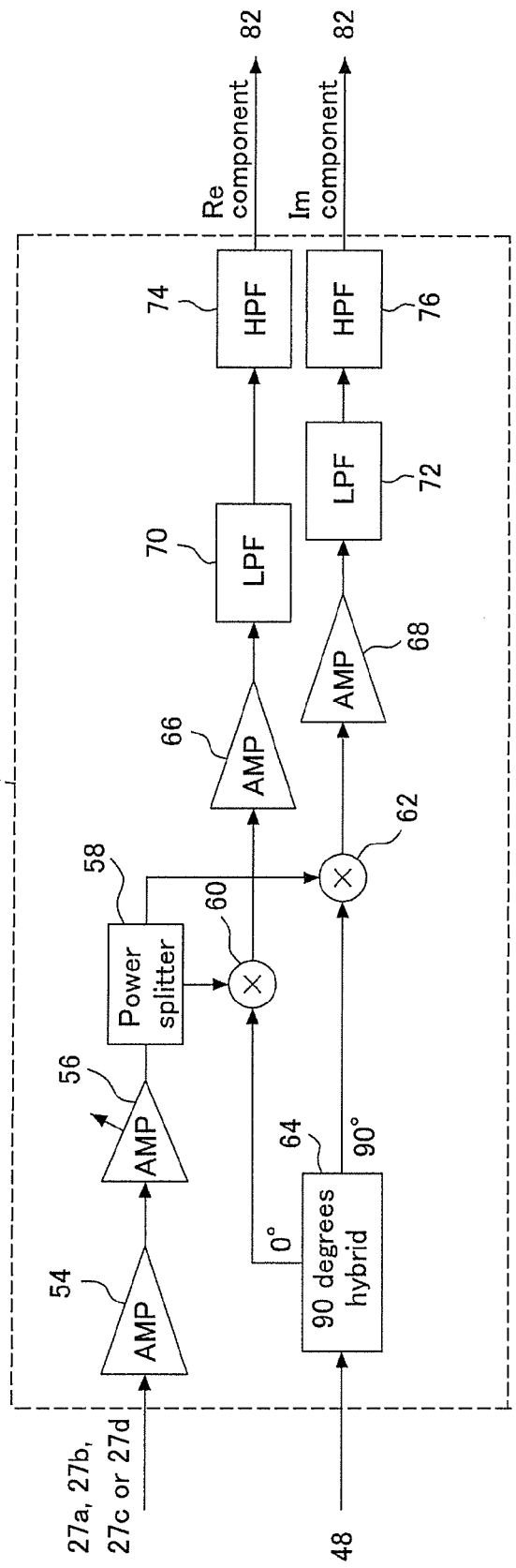
FIG. 3 is a diagram for explaining the structure of a signal processing unit of the flow cytometer illustrated in FIG. 1.

FIG. 3 is a diagram illustrating the structure of each of the processing circuits 52a, 52b, 52c, and 52d.

Each of the processing circuits 52a to 52d includes an amplifier 54 that amplifies a fluorescent signal (light-receiving signal), a variable amplifier 56, a power splitter 58 that splits an amplified fluorescent signal (light-receiving signal), RF mixers (first mixers) 60 and 62, a 90 degrees hybrid phase shifter 64, amplifiers 66 and 68, low-pass filters (first low-pass filters) 70 and 72, and high-pass filters 74 and 76. The RF mixers of the signal processing channel 4 correspond to third mixers, and the low-pass filters of the signal processing channel 4 correspond to third low-pass filters.

The fluorescent signal (light-receiving signal) sent from each of the photoelectric converters 27a to 27c (27d) is amplified by the amplifier 54 and is further amplified to a desired level by the variable amplifier 56. Further, the fluorescent signal (light-receiving signal) is split into two signals by the power splitter 58 and sent to the RF mixers 60 and 62.

It is to be noted that the RF mixers in each of the processing circuits 52a, 52b, and 52c of the signal processing channels 1, 2, and 3 correspond to first mixers of the fluorescence detection device according to the present invention, and the RF mixers 60 and 62 in the processing circuit 52d of the signal processing channel 4 correspond to third mixers of the fluorescence detection device according to the present invention.

On the other hand, the reference signal generated by the oscillator 48 is supplied to the 90 degrees hybrid phase shifter 64 to generate a 90 degrees phase-shifted reference signal and a reference signal not phase-shifted (with a phase shift of) 0°). The 90 degrees phase-shifted reference signal by the 90 degrees hybrid phase-shifter 64 is supplied to the RF mixer 62. On the other hand, the reference signal not phase-shifted is supplied to the RF mixer 60.

Each of the RF mixers 60 and 62 performs mixing processing to mix the supplied reference signal and the supplied fluorescent signal (light-receiving signal). As the RF mixers 60 and 62, active mixers or passive mixers such as double-balanced mixers are employed.

In the present embodiment, the reference signal is phase-shifted by 90 degrees and supplied to the RF mixer 62, but the fluorescent signal (light-receiving signal) may be phase-shifted by 90 degrees instead of the reference signal.

The amplifier 66 amplifies a mixed signal generated by the RF mixer 60 by mixing the reference signal and the fluorescent signal (light-receiving signal), and the amplifier 68 amplifies a mixed signal generated by the RF mixer 62 by mixing the reference signal and the fluorescent signal (light-receiving signal).

Each of the low-pass filters 70 and 72 removes, from the mixed signal obtained by the mixing processing, a high-frequency component including a sum frequency of the frequency of the reference signal and the frequency of the fluorescent signal (light-receiving signal) and transmits a low-frequency component including a difference frequency between the frequency of the reference signal and the frequency of the fluorescent signal (light-receiving signal), and therefore the cut-off frequency of each of the low-pass filters 70 and 72 is set to, for example, a value lower than the above-mentioned sum frequency but higher than the above-mentioned difference frequency. This makes it possible to allow the low-pass filter 70 to output a real part component (Re component) as information about the phase delay of the fluorescent signal (light-receiving signal) and to allow the low-pass filter 72 to output an imaginary part component (Im component) as information about the phase delay of the fluorescent signal (light-receiving signal). The signal of the Re component is sent to the high-pass filter 74 and the signal of the Im component is sent to the high-pass filter 76. The high-pass filter 74 removes a DC component from the signal of the Re component and the high-pass filter 76 removes a DC component from the signal of the Im component. This makes it possible to remove a DC component offset contained in the mixed signal outputted by each of the RF mixers 60 and 62 while the information about the phase delay of the fluorescent signal (light-receiving signal) is kept contained in an AC component. The signal of the Re component that has passed through the high-pass filter 74 and the signal of the Im component that has passed through the high-pass filter 76 are sent to the AD conversion board 82 of the analyzing device 80.

It is to be noted that the low-pass filters in each of the processing circuits 52a, 52b, and 52c of the signal processing channels 1, 2, and 3 correspond to first low-pass filters of the fluorescence detection device according to the present invention, and the low-pass filters (not illustrated) in the processing circuit 52d of the signal processing channel 4 correspond to third low-pass filters of the fluorescence detection device according to the present invention.

As described above, the frequency of the modulation signal is different from that of the reference signal. Thus, the frequency of the fluorescent signal (light-receiving signal) is also different from that of the reference signal. Therefore, the signal of the real part component (Re component) outputted from the low-pass filter 70 and the signal of the imaginary part component (Im component) outputted from the low-pass filter 72 are each an AC component signal having a difference frequency between the frequency of the modulation signal and the frequency of the reference signal. This signal contains information about phase delay. In the case of a conventional method, the modulation signal and the reference signal have the same frequency, and therefore a signal outputted from each of the low-pass filters 70 and 72 is a DC component having a constant value. As described above, a DC component offset is superimposed on a result obtained by mixing performed by the RF mixer, and therefore when information about phase delay is a DC component, the analyzing device 80 cannot determine fluorescence relaxation time with a high degree of accuracy. For this reason, in the flow cytometer 10, the frequency of the modulation signal and the frequency of the reference signal are set so that information about phase delay obtained as a result of mixing is contained in an AC component.

The real part component (Re component) and the imaginary part component (Im component), which are in AC components, are sent to the analyzing device 80.

The analyzing device 80 includes the AD conversion board 82 (see FIG. 1) and the analyzing device main body (computer) 84. The AD conversion board 82 converts the real part component (Re component) and the imaginary part component (Im component) sent from each of the signal processing channels 1 to 4 into digital signals.

The AD conversion board 82 starts AD conversion of the real part component (Re component) and the imaginary part component (Im component) in response to the signal sent from the light-receiving unit 24 as a trigger signal. Then, the digitized real part component (Re component) and the digitized imaginary part component (Im component) are supplied to the analyzing device main body 84. The analyzing device 80 starts analysis using the digitized real part component (Re component) and the digitized imaginary part component (Im component).

The analyzing device main body 84 determines the phase delay angle of fluorescence relative to laser light based on the real part component (Re component) and the imaginary part component (Im component), and further determines fluorescence relaxation time from the phase delay angle. Based on the thus determined fluorescence relaxation time, the type of fluorochrome, from which the fluorescent signal outputted from the light-receiving unit 26 is derived, is identified.

The analyzing device main body 84 determine the wavelength of fluorescence from which the fluorescence relaxation time is derived, by finding which signal processing channel outputting the real part component (Re component) and the imaginary part component (Im component) is associated with the determined fluorescence relaxation time. The fluorescence relaxation time of fluorescence emitted from a fluorochrome depends on the type of fluorochrome. Therefore, the analyzing device main body 84 can identify the type of fluorochrome, from which the fluorescence is derived, by determining the value of fluorescence relaxation time and finding which signal processing channel is associated with the determined fluorescence relaxation time. Further, the type of fluorochrome attached to the sample 12 depends on the type of sample 12, and therefore the analyzing device main body 84 can identify the type of sample 12 that has passed through the measurement point by identifying the type of fluorescence. In a case where different two types of biological substances in the sample 12 are biologically bound, fluorescence emitted from a fluorochrome attached to one of the two types of biological substances and fluorescence emitted from another fluorochrome attached to the other biological substance are detected at almost the same time. In this case, the analyzing device main body 84 can identify the types of biological substances biologically bound to each other by identifying the types of fluorescence based on the values of fluorescence relaxation time. Such analysis is performed per each sample 12 passing through the measurement point, and therefore the analyzing device main body 84 can analyze the sample 12 comprehensively by statistically processing a plurality of obtained results.

The analyzing device main body 84 constitutes a fluorescence detection unit that calculates fluorescence relaxation time in the present invention, and is composed of a computer.

Figure 4:
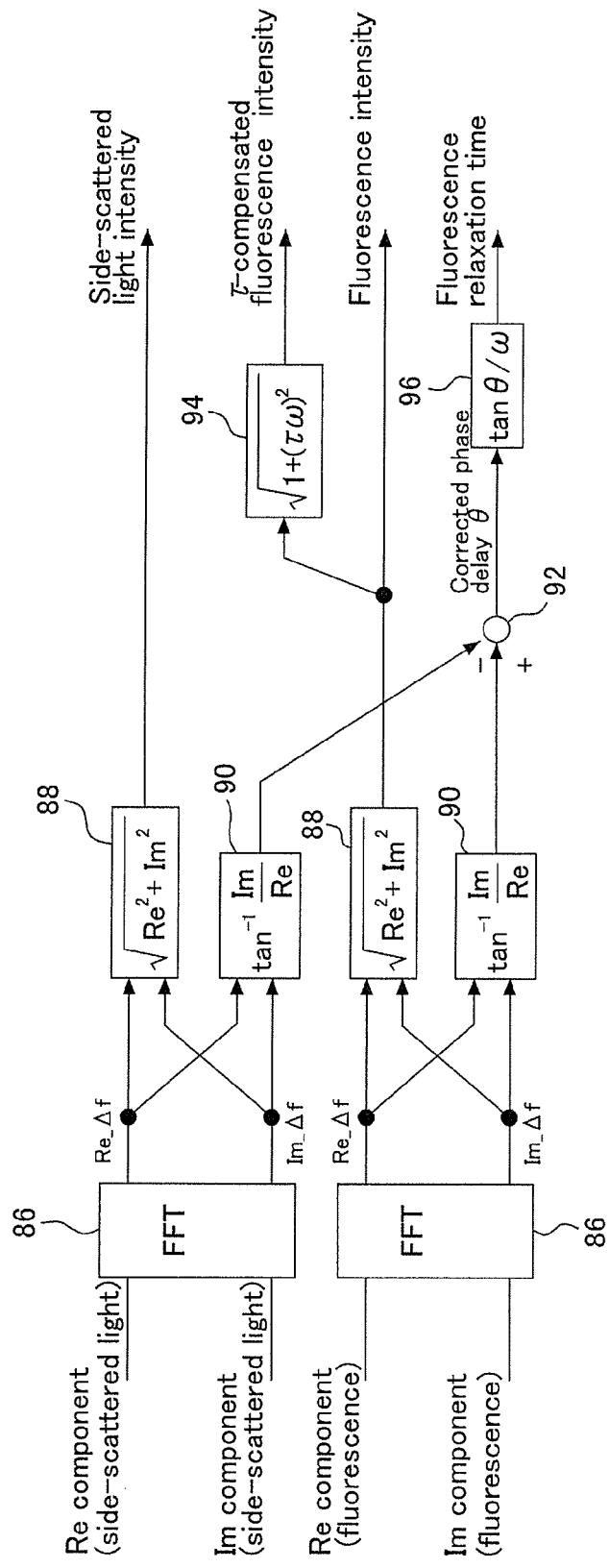
FIG. 4 is a diagram for explaining the contents of processing performed by an analyzing device of the flow cytometer illustrated in FIG. 1.

FIG. 4 is a diagram for explaining an example of contents of processing performed by the analyzing device main body 84.

The analyzing device main body 84 performs the processing illustrated in FIG. 4 after the real part component (Re component) and the imaginary part component (Im component) outputted from each of the signal processing channels are converted into digital data by the AD conversion board 82. The processing is performed by software.

Each of the contents of processing performed by software is modularized by a subprogram or subroutine. More specifically, the analyzing device main body 84 includes an FFT processing module 86, an amplitude calculation module 88, a phase calculation module 90, a phase delay calculation module 92, a compensated-fluorescence intensity calculation module 94, and a fluorescence relaxation time calculation module 96.

FIG. 4 illustrates, as an example of contents of processing, contents of processing of the real part component (Re component) and imaginary part component (Im component) of fluorescence sent from the processing circuit 52a and contents of processing of the real part component (Re component) and imaginary part component (Im component) of side-scattered light of laser light L sent from the processing circuit 52d. The example of contents of processing illustrated in FIG. 4 does not include contents of processing of the real part component (Re component) and the imaginary part component (Im component) sent from each of the processing circuits 52b and 52c. The contents of processing of the real part component (Re component) and the imaginary part component (Im component) sent from each of the processing circuits 52b and 52c are the same as the contents of processing of the real part component (Re component) and the imaginary part component (Im component) sent from the processing circuit 52a, and are therefore not illustrated in FIG. 4 and the description thereof will not be repeated here.

The real part component (Re component) and the imaginary part component (Im component), which relate to the phase delay of side-scattered light and are sent from the processing circuit 52d, are sent to the FFT processing module 86 and subjected to FFT processing. The real part component (Re component) and imaginary part component (Im component) of fluorescence are also sent to the FFT processing module 86 and subjected to FFT processing.

The FFT processing module 86 determines, from the real part component (Re component), the value of the real part component corresponding to a difference frequency $\Delta f$ between the modulation signal and the reference signal (Re_$\Delta f$) and determines, from the imaginary part component (Im component), the value of the imaginary part component corresponding to the difference frequency $\Delta f$ (Im_$\Delta f$). The thus determined value of the real part component (Re_$\Delta f$) and value of the imaginary part component (Im_$\Delta f$) are sent to the amplitude calculation module 88. The value of the real part component (Re_$\Delta f$) and the value of the imaginary part component (Im_$\Delta f$) obtained from the fluorescent signal correspond to a first signal component corresponding to a difference frequency in the present invention, and the value of the real part component (Re_$\Delta f$) and the value of the imaginary part component (Im_$\Delta f$) obtained from the light-receiving signal correspond to a second signal component corresponding to a difference frequency in the present invention.

The amplitude calculation module 88 calculates the square-root of sum of squares of the value of the real part component (Re_$\Delta f$) and the value of the imaginary part component (Im_$\Delta f$) and outputs the calculated result as intensity. That is, the amplitude calculation module 88 outputs side-scattered light intensity and fluorescence intensity.

Further, the value of the real part component (Re_$\Delta f$) and the value of the imaginary part component (Im_$\Delta f$), which are obtained by FFT processing and correspond to the difference frequency, are sent to the phase calculation module 90. The phase calculation module 90 calculates $\tan^{-1}(\text{Im}\_\Delta f/\text{Re}\_\Delta f)$ to determine the phase delay of side-scattered light and the phase delay of fluorescence.

Further, the phase delay calculation module 92 determines the corrected phase delay of the fluorescent signal relative to the reference signal by subtracting the phase delay of side-scattered light determined by the phase calculation module 90 from the phase delay of fluorescence determined by the phase calculation module 90. The reason why the phase delay of the fluorescent signal is corrected is to eliminate a phase shift caused by the difference between the transmission line of the reference signal and the transmission line of the fluorescent signal or the light-receiving signal derived from side-scattered light.

Then, the fluorescence relaxation time calculation module 96 calculates $\tan\theta/\omega$ using the corrected phase delay $\theta$, and outputs the calculated result as fluorescence relaxation time $\tau$. Here, $\omega$ is $2\pi f$ and f represents the frequency of the modulation signal.

The reason why the value of $\tan\theta/\omega$ can be regarded as fluorescence relaxation time $\tau$ is that fluorescence is emitted according to a first order lag response during a fluorescence relaxation process.

Further, the compensated-fluorescence intensity calculation module 94 calculates $(1+(\tau\omega)^2)^{(1/2)}$, and this calculated value is multiplied by the amplitude of fluorescence calculated by the amplitude calculation module 88 to determine $\tau$-compensated fluorescence intensity.

As described above, the analyzing device main body 84 calculates side-scattered light intensity, fluorescence intensity, fluorescence relaxation time $\tau$, and $\tau$-compensated fluorescence intensity, and performs statistical processing and analysis using the calculated results. As a matter of course, it is not always necessary to calculate all the side-scattered light intensity, fluorescence intensity, fluorescence relaxation time $\tau$, and $\tau$-compensated fluorescence intensity to perform statistical processing and analysis using the calculated results. The analyzing device main body 84 preferably calculates at least fluorescence relaxation time $\tau$ to perform statistical processing and analysis using the fluorescence relaxation time $\tau$. It is to be noted that the side-scattered light intensity greatly varies depending on the structure of the sample 12, and therefore can be used as an indicator indicating the complexity of the structure of the sample 12.

The flow cytometer 10 has the above-described structure. In the flow cytometer 10, the oscillator 46 generates a clock signal, and the oscillator 47 generates a modulation signal in synchronization with the clock signal generated by the oscillator 46, and the oscillator 48 generates a reference signal in synchronization with the clock signal.

Therefore, a noise component contained in the modulation signal generated by the oscillator 47 and a noise component contained in the reference signal generated by the oscillator 48 are independent of each other, which makes it possible to, even when the fluorescent signal is mixed with the reference signal by each of the RF mixers 60 and 62, prevent a large noise component from being contained in the resulting mixed signal. This is because, unlike a conventional case, it is possible to prevent a fluorescent signal containing a noise component from being multiplied by a reference signal containing a noise component at the same time as the fluorescent signal.

In the signal processing device 20 of such a flow cytometer 10, first, the oscillator 47 generates a modulation signal having a predetermined frequency in synchronization with the clock signal generated by the oscillator 46. Then, the modulation signal is subjected to predetermined processing by the laser driver 34, and is supplied to the laser light source unit 23. The laser light source unit 23 emits laser light L, whose intensity has been modulated at the frequency of the modulation signal, toward the measurement point. The laser light L is focused by a lens system (not illustrated) into a laser beam having a diameter of several tens of micrometers as measured at the measurement point.

In this state, the samples 12 are allowed to flow through the tube 30 so that a flow is formed. The flow has a diameter of, for example 100 μm and a flow rate of, for example, 1 to 10 m/sec.

The laser light source unit 23 emits laser light L toward the measurement point. The light-receiving unit 24 generates a detection signal indicating the passage of the sample 12 through the measurement point and then sends this detection signal to the analyzing device 80 as a trigger signal.

In response to the trigger signal, the oscillator 46 generates a reference signal in synchronization with the clock signal generated by the oscillator 48.

The signal processing unit 42 performs mixing processing and low-pass filtering according to the signal processing circuit illustrated in FIG. 3 using the fluorescent signals and the light-receiving signal sent from the photoelectric converters 27a to 27d and the reference signal. In this way, the signal processing unit 42 generates a real part component (Re component) and an imaginary part component (Im component) which include information about the phase delay of each of the fluorescent signals and the light-receiving signal derived from side-scattered light.

Here, the frequency of the modulation signal for modulating laser light L is, for example 10 to 50 MHz, and a difference frequency between the modulation signal and the reference signal is 100 kHz to 1 MHz. The frequency of the reference signal may be either lower or higher than that of the modulation signal.

The calculated real part component (Re component) and imaginary part component (Im component) are sent to the analyzing device 80.

The analyzing device 80 performs AD conversion to digitize the signal of the real part component (Re component) and the signal of the imaginary part component (Im component) sent from the signal processing unit 42. Then, the analyzing device 80 performs the processing illustrated in FIG. 4 to calculate side-scattered light intensity, fluorescence intensity, fluorescence relaxation time $\tau$, and $\tau$-compensated fluorescence intensity. The calculated results are used for statistical processing and analysis of the sample 12. It is to be noted that the analyzing device 80 calculates fluorescence relaxation time using the formula $\tan \theta/\omega$ based on the phase delay $\theta$ of the fluorescent signal relative to the phase delay of the light-receiving signal derived from side-scattered light.

MODIFIED EXAMPLE 1

Figure 5:
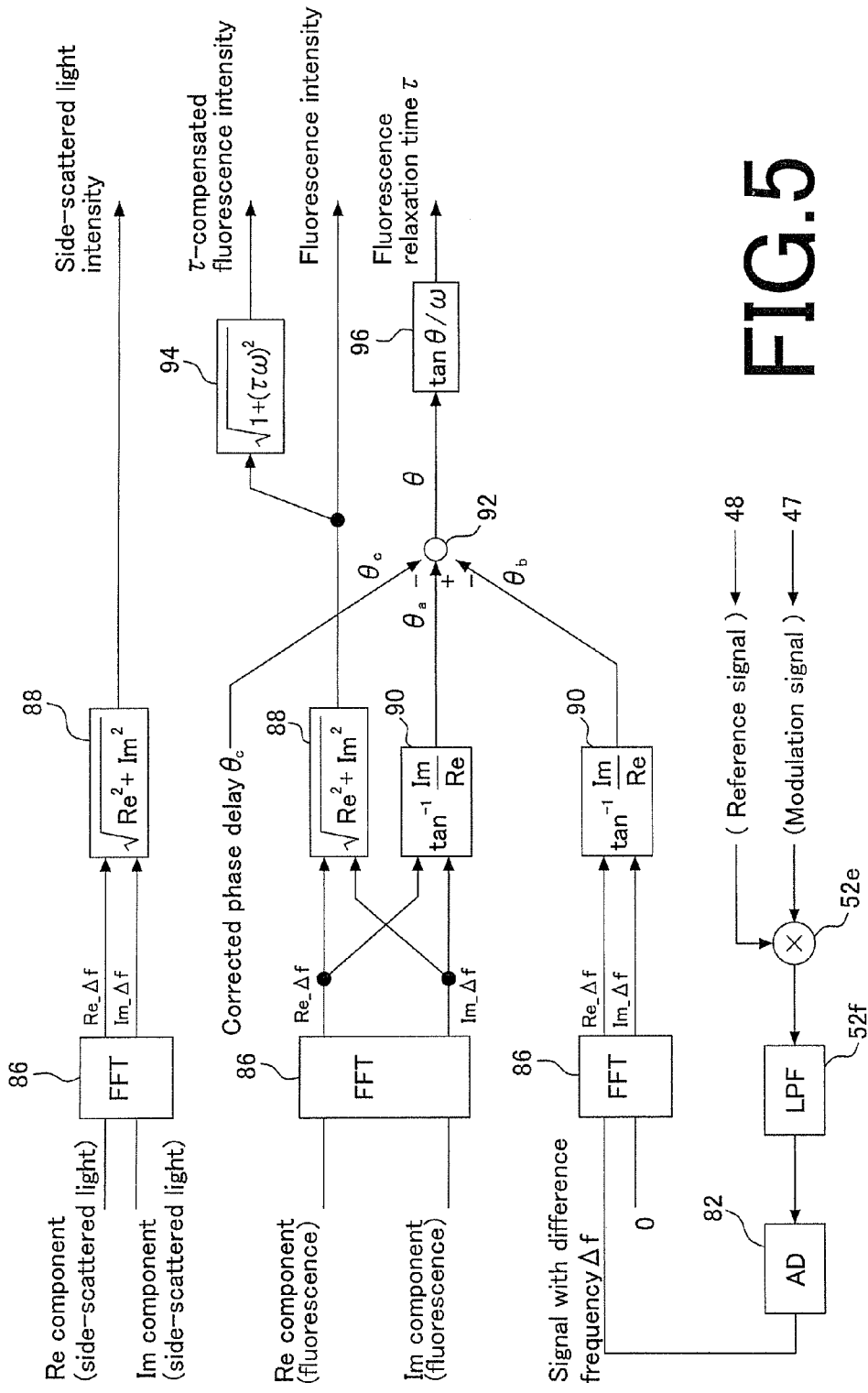
FIG. 5 is a diagram for explaining another example of contents of processing performed by the analyzing device which are different from the contents of processing illustrated in FIG. 4.

FIG. 5 is a diagram for explaining an example of contents of processing performed by the analyzing device main body 84 which are different from the contents of processing illustrated in FIG. 4. The processing illustrated in FIG. 5 is performed using the FFT processing module 86, the amplitude calculation module 88, the phase calculation module 90, the phase delay calculation module 92, the compensated-fluorescence intensity calculation module 94, and the fluorescence relaxation time calculation module 96 having their respective functions illustrated in FIG. 4.

In order to perform the processing illustrated in FIG. 5, a circuit including an RF mixer (second mixer) 52e and a low-pass filter (second low-pass filter) 52f is provided in the signal processing unit 42. The RF mixer 52e performs mixing processing to mix the modulation signal generated by the oscillator 47 and the reference signal generated by the oscillator 48. The low-pass filter 52f performs, on a mixed signal obtained by the mixing processing using the RF mixer 52e, low-pass filtering using a cut-off frequency lower than the sum frequency of the frequency of the modulation signal and the frequency of the reference signal but higher than the difference frequency between the frequency of the modulation signal and the frequency of the reference signal, and outputs a sine-wave signal (second reference signal) having the difference frequency as its frequency. At this time, the signal outputted from the circuit is supplied to the analyzing device main body 84 via the AD conversion board 82.

In the case of the processing illustrated in FIG. 5, first, the FFT processing module 86 processes the real part component (Re component) and imaginary part component (Im component) of the light-receiving signal calculated by the signal-processing channel 4 to determine the value of the real part component (Re_$\Delta$f) at the difference frequency $\Delta$f and the value of the imaginary part component (Im_$\Delta$f) at the difference frequency $\Delta$f. From these two values, the amplitude calculation module 88 calculates the amplitude of the light-receiving signal derived from side-scattered light and outputs the calculated amplitude as side-scattered light intensity.

On the other hand, the FFT processing module 86 processes the real part component (Re component) and imaginary part component (Im component) of the fluorescent signal obtained by the signal processing channel 1 to determine the value of the real part component (Re_$\Delta$f) at the difference frequency $\Delta$f and the value of the imaginary part component (Im_$\Delta$f) at the difference frequency $\Delta$f. From these two values, the amplitude calculation module 88 calculates fluorescence intensity and the phase calculation module 90 calculates the phase delay $\theta_a$ of the fluorescent signal. The real part component (Re component) and imaginary part component (Im component) of the fluorescent signal obtained by each of the signal processing channels 2 and 3 are processed in the same manner as those of the fluorescent signal obtained by the signal processing channel 1, and therefore the description thereof will not be repeated. FIG. 5 does not illustrate the processing of the fluorescent signals obtained by the signal processing channels 2 and 3, either.

As described above, the analyzing device main body 84 receives AD-converted data of the signal having the difference frequency $\Delta$f obtained by mixing the modulation signal and the reference signal and subjecting the resulting mixed signal to low-pass filtering. Then, the FFT processing module 86 determines the value of the real part component (Re_$\Delta$f) at the difference frequency $\Delta$f and the value of the imaginary part component (Im_$\Delta$f) at the difference frequency $\Delta$f. From these two values, the phase calculation module 90 calculates a phase $\theta_b$.

Then, from the phase delay $\theta_a$ of the fluorescent signal, the phase $\theta_b$, and a correction phase $\theta_c$ previously stored in the analyzing device main body 84, the phase delay calculation module 92 calculates $\theta_a - \theta_b - \theta_c$ to determine the corrected phase delay $\theta$ of the fluorescent signal relative to the reference signal. The reason why the phase $\theta_b$ is subtracted from the phase delay $\theta_a$ of the fluorescent signal is to eliminate phase delay due to the transmission delay time of the signal transmitted to the signal processing unit 42 and delay time caused by processing.

Here, the correction phase (correction amount) $\theta_c$ is previously stored in the analyzing device main body 84. The correction phase $\theta_c$ stored in the analyzing device main body 84 is determined in the following manner. A known fluorochrome that emits fluorescence with a known fluorescence relaxation time is set as the sample 12, and fluorescence emitted from the sample 12 is measured. At this time, the correction phase $\theta_c$ is determined so that fluorescence relaxation time determined from a corrected phase delay represented as $\theta_a - \theta_b - \theta_c$ becomes equal to the known fluorescence relaxation time of the fluorochrome.

That is, the correction phase $\theta_c$ is a correction amount for calibrating a measurement result so that the measurement result becomes equal to the known fluorescence relaxation time.

The corrected phase delay θ is sent to the fluorescence relaxation time calculation module 96. The fluorescence relaxation time calculation module 96 calculates tan θ/ω to determine fluorescence relaxation time τ.

Further, the compensated-fluorescence intensity calculation module 94 calculates $(1+(\tau\omega)^2)^{(1/2)}$ to determine τ-compensated fluorescence intensity.

In this way, the analyzing device main body 84 calculates side-scattered light intensity, τ-compensated fluorescence intensity, fluorescence intensity, and fluorescence relaxation time τ, and performs statistical processing and analysis of the sample 12 using the calculated results.

MODIFIED EXAMPLE 2

Figure 6:
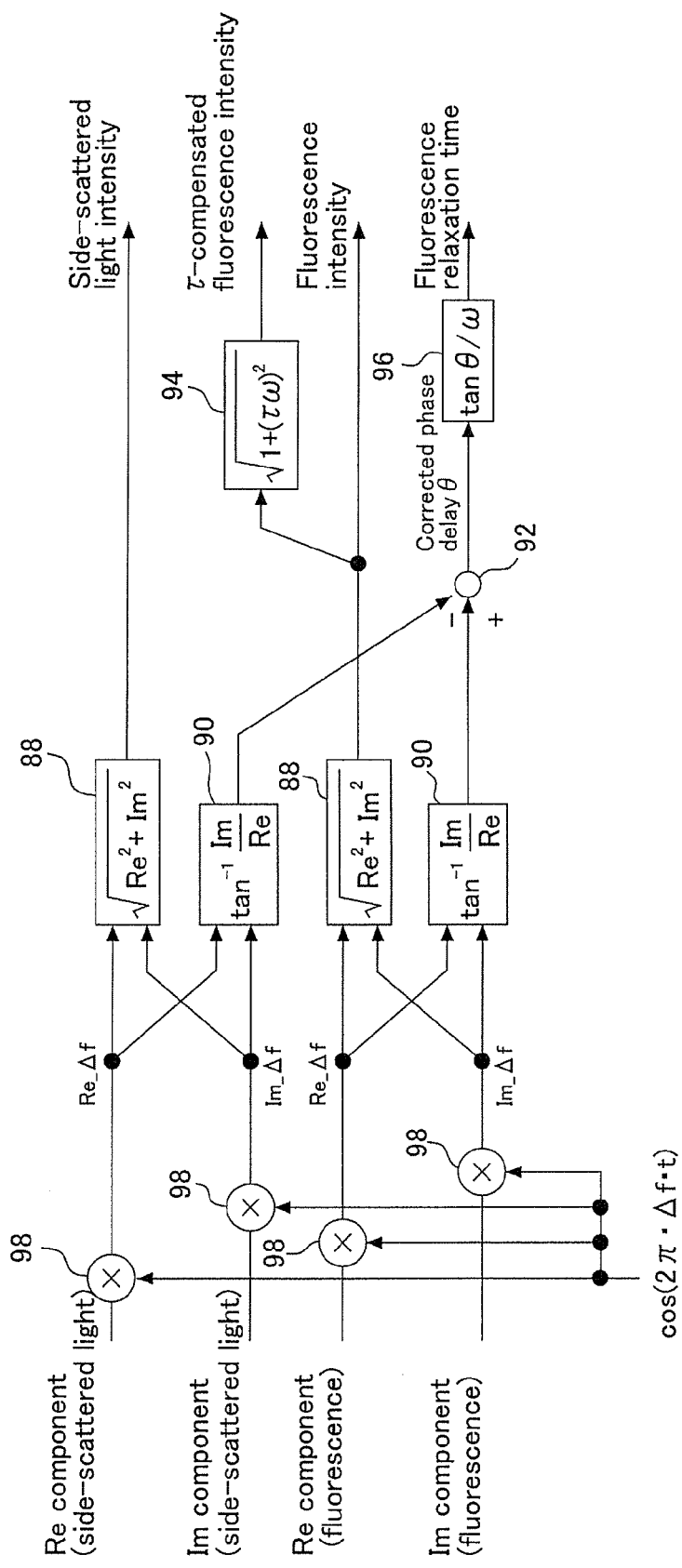
FIG. 6 is a diagram for explaining another example of contents of processing performed by the analyzing device which are different from the contents of processing illustrated in FIGS. 4 and 5.

FIG. 6 is a diagram for explaining an example of contents of processing performed by the analyzing device main body 84 which are different from the contents of processing illustrated in FIGS. 4 and 5. The processing illustrated in FIG. 6 is performed using the amplitude calculation module 88, the phase calculation module 90, the phase delay calculation module 92, the compensated-fluorescence intensity calculation module 94, and the fluorescence relaxation time calculation module 96, all of which have their respective functions illustrated in FIG. 4, and a mixing processing module 98.

In the case of the processing illustrated in FIG. 6, unlike the processing illustrated in FIG. 4 in which the value of the real part component (Re_Δf) at the difference frequency Δf and the value of the imaginary part component (Im_Δf) at the difference frequency Δf are determined by the FFT processing module 86, the real part component (Re component) and imaginary part component (Im component) of the fluorescent signal and the real part component (Re component) and imaginary part component (Im component) of the light-receiving signal derived from side-scattered light are each mixed with cos(2π·Δf·t), which is separately generated by the analyzing device main body 84, by the mixing processing module 98 to determine the values of the real part component (Re_Δf) at the difference frequency Δf and the values of the imaginary part component (Im_Δf) at the difference frequency Δf.

The mixing processing module 98 is performed by software stored in the analyzing device main body 84 that is a computer, and therefore unlike the case where mixing processing is performed by the RF mixers 60 and 62, a DC component offset is not generated. This makes it possible to perform mixing processing with a high degree of accuracy.

It is to be noted that the mixing processing using the RF mixers 60 and 62 may be performed by the analyzing device 80 to prevent the generation of a DC component offset. However, in this case, an expensive AD conversion board that performs AD conversion on the fluorescent signal or light-receiving signal whose intensity is modulated at 10 to 50 MHz is used as the AD conversion board 82 of the analyzing device 80, but such a board is too expensive to be of practical use.

Each of the values of the real part component (Re_Δf) at the difference frequency Δf calculated by the mixing processing module 98 is sent to the amplitude calculation module 88 and the phase calculation module 90, and each of the values of the imaginary part component (Im_Δf) at the difference frequency Δf calculated by the mixing processing module 98 is sent to the amplitude calculation module 88 and the phase calculation module 90, and the subsequent processing is the same as that illustrated in FIG. 4, and therefore the description thereof will not be repeated.

In this way, the analyzing device main body 84 calculates side-scattered light intensity, τ-compensated fluorescence intensity, fluorescence intensity, and fluorescence relaxation time τ, and performs statistical processing and analysis of the sample 12 using the calculated results.

MODIFIED EXAMPLE 3

Figure 7:
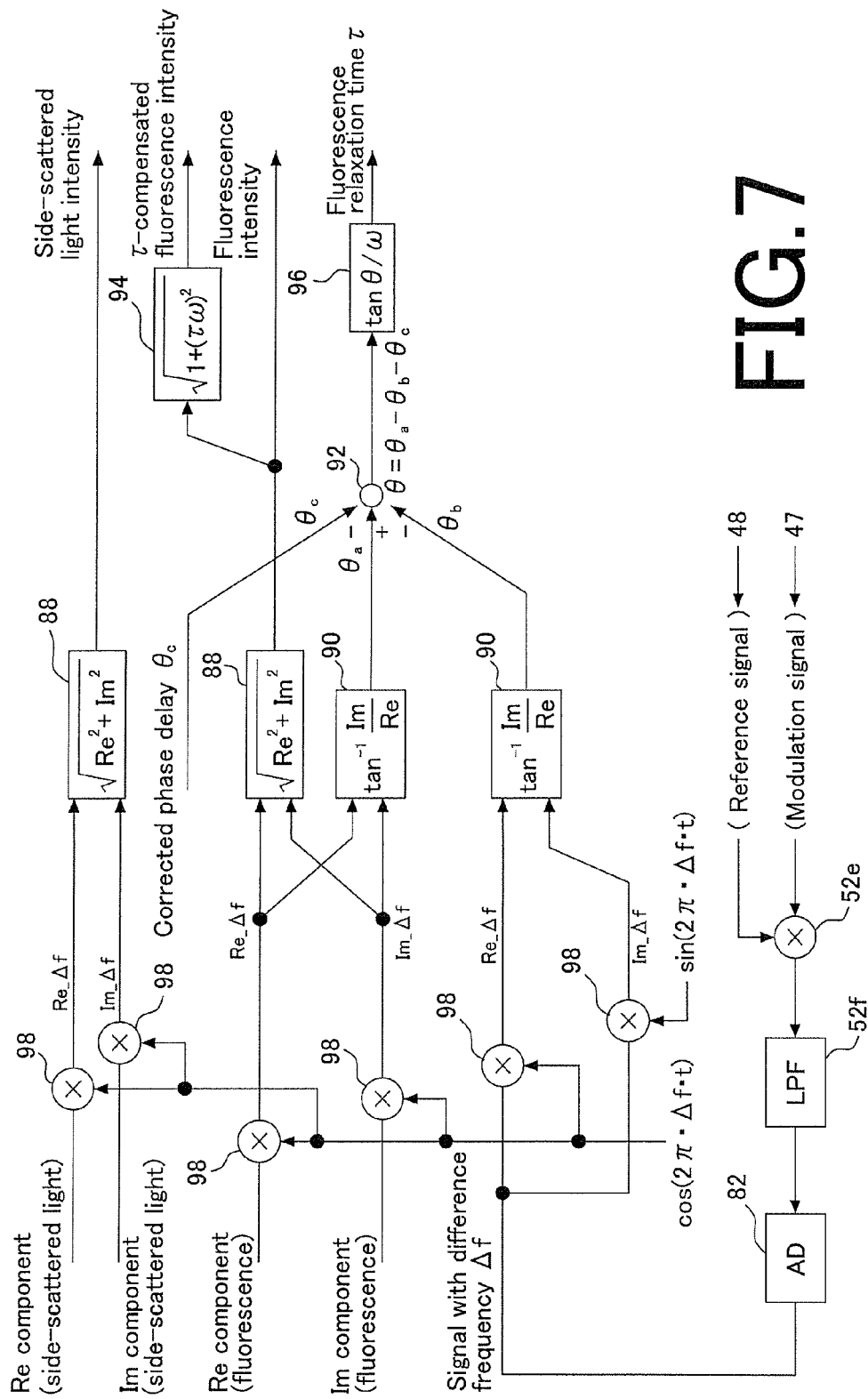
FIG. 7 is a diagram for explaining another example of contents of processing performed by the analyzing device which are different from the contents of processing illustrated in FIGS. 4 to 6.

FIG. 7 is a diagram for explaining an example of contents of processing performed by the analyzing device main body 84 which are different from the contents of processing illustrated in FIGS. 4, 5, and 6. The processing illustrated in FIG. 7 is performed using the amplitude calculation module 88, the phase calculation module 90, the phase delay calculation module 92, and the compensated-fluorescence intensity calculation module 94, and the fluorescence relaxation time calculation module 96, all of which have their respective functions illustrated in FIG. 5, and the mixing processing module 98 illustrated in FIG. 6.

In the case of the processing illustrated in FIG. 7, unlike the processing illustrated in FIG. 5 in which the value of the real part component (Re_Δf) at the difference frequency Δf and the value of the imaginary part component (Im_Δf) at the difference frequency Δf are determined by the FFT processing module 86, the real part component (Re component) and imaginary part component (Im component) of the fluorescent signal and the real part component (Re component) and imaginary part component (Im component) of the light-receiving signal derived from side-scattered light are each mixed with cos(2π·Δf·t), which is generated by the analyzing device main body 84, by the mixing processing module 98 of the analyzing device main body 84 to determine the values of the real part component (Re_Δf) at the difference frequency Δf and the values of the imaginary part component (Im_Δf) at the difference frequency Δf. Further, the mixing processing module 98 of the analyzing device main body 84 mixes cos (2π·Δf·t) generated by the analyzing device main body 84, sin(2π·Δf·t) separately generated by the analyzing device main body 84, and the signal having the difference frequency Δf. As illustrated in FIG. 7, the signal having the difference frequency Δf is generated by mixing the modulation signal and the reference signal by the RF mixer 52e, subjecting the resulting mixed signal to low-pass filtering using the low-pass filter 52f, and AD-converting the mixed signal. The value of the real part component (Re_Δf) at the difference frequency Δf of the signal having the difference frequency Δf and the value of the imaginary part component (Im_Δf) at the difference frequency Δf of the signal having the difference frequency Δf are determined.

The value of the real part component (Re_Δf) of the signal having the difference frequency Δf and the value of the imaginary part component (Im_Δf) of the signal having the difference frequency Δf calculated by the mixing processing module 98 are sent to the phase calculation module 90. The subsequent processing is the same as that illustrated in FIG. 5, and is therefore the description thereof will not be repeated.

In this way, the analyzing device main body 84 calculates side-scattered light intensity, τ-compensated fluorescence intensity, fluorescence intensity, and fluorescence relaxation time τ, and performs statistical processing and analysis of the sample 12 using the calculated results.

MODIFIED EXAMPLE 4

Figure 8:
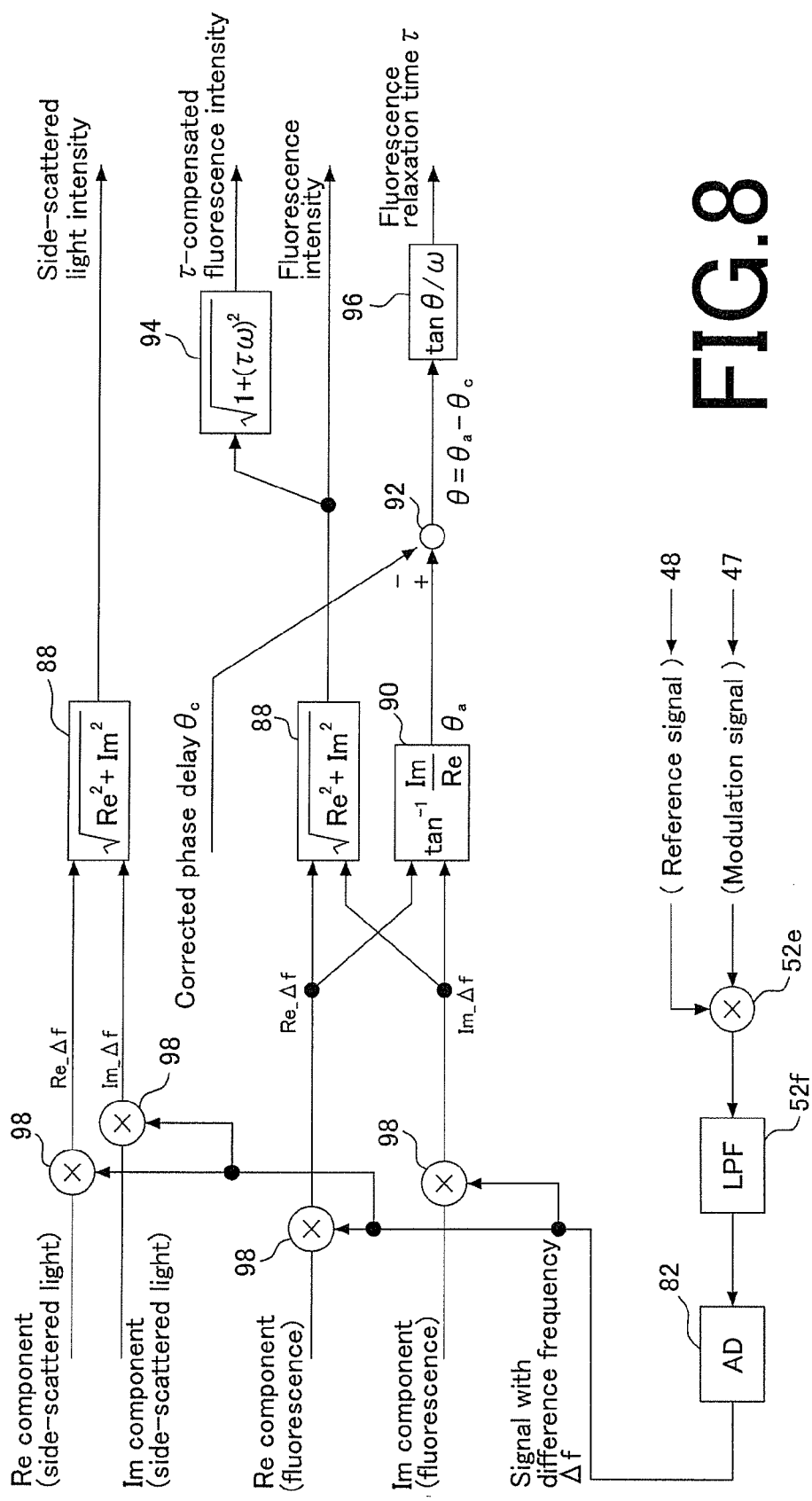
FIG. 8 is a diagram for explaining another example of contents of processing performed by the analyzing device which are different from the contents of processing illustrated in FIGS. 4 to 7.

FIG. 8 is a diagram for explaining an example of contents of processing performed by the analyzing device main body 84 which are different from the contents of processing illustrated in FIGS. 4 to 7. The processing illustrated in FIG. 8 is performed using the amplitude calculation module 88, the phase calculation module 90, the phase delay calculation module 92, and the compensated-fluorescence intensity calculation module 94, and the fluorescence relaxation time calculation module 96 illustrated in FIG. 5 and the mixing processing module 98 illustrated in FIG. 6.

In order to perform the processing illustrated in FIG. 8, as in the case of the processing illustrated in FIG. 5, a signal outputted from a circuit having the RF mixer 52e and the low-pass filter 52f illustrated in FIG. 8 is supplied to the analyzing device main body 84 via the AD conversion board 82, the circuit calculating the signal having the difference frequency Δf by mixing the modulation signal and the reference signal and subjecting the resulting mixed signal to low-pass filtering in the signal processing unit 42.

In the case of the processing illustrated in FIG. 8, first, the real part component (Re component) and imaginary part component (Im component) of each of the fluorescence signal and the light-receiving signal obtained by the signal processing channel 4 are each mixed with the signal having the difference frequency Δf by the mixing processing module 98 to determine the value of the real part component (Re_Δf) at the difference frequency Δf and the value of the imaginary part component (Im_Δf) at the difference frequency Δf. From these two values, the amplitude calculation module 88 calculates each of the amplitude of the light-receiving signal derived from side-scattered light and the amplitude of the fluorescent signal and outputs these amplitudes as side-scattered light intensity and fluorescence intensity. Further, the phase calculation module 90 calculates a phase $\theta_a$ of the fluorescent signal from the value of the real part component (Re_Δf) of the fluorescent signal and the value of the imaginary part component (Im_Δf) of the fluorescent signal.

Then, from the calculated phase $\theta_a$ of the fluorescent signal and a correction phase $\theta_c$ previously stored in the analyzing device main body 84, the fluorescence relaxation time calculation module 96 calculates $\theta_a - \theta_c$ to determine the corrected phase delay θ of the fluorescent signal relative to the reference signal.

Here, the correction phase (correction amount) $\theta_c$ is previously stored in the analyzing device main body 84. The correction phase $\theta_c$ stored in the analyzing device main body 84 is determined in the same manner as in the case of the correction phase $\theta_c$ illustrated in FIG. 5. That is, a known fluorochrome that emits fluorescence with a known fluorescence relaxation time is set as the sample 12, and fluorescence emitted from the sample 12 is measured. At this time, the correction phase $\theta_c$ is determined so that fluorescence relaxation time τ determined from a corrected phase delay represented as $\theta_a - \theta_c$ becomes equal to the known fluorescence relaxation time of the fluorochrome. That is, the correction phase $\theta_c$ is a correction amount for calibrating a measurement result so that the measurement result becomes equal to the known fluorescence relaxation time.

It is to be noted that the processing illustrated in FIG. 8 is different from that illustrated in FIG. 5 in that the phase $\theta_b$ is not used to calculate the phase delay θ. This is because the value of the real part component (Re_Δf) of the fluorescent signal and the value of the imaginary part component (Im_Δf) of the fluorescent signal, each obtained by mixing processing with the signal having the difference signal Δf, have information in which phase delay caused by signal transmission delay time and signal processing delay time is removed.

Therefore, the corrected phase delay θ can be determined by calculating $\theta_a - \theta_c$.

The subsequent processing is the same as that illustrated in FIG. 5, and therefore the description thereof will not be repeated.

In this way, the analyzing device main body 84 calculates side-scattered light intensity, τ-compensated fluorescence intensity, fluorescence intensity, and fluorescence relaxation time τ, and performs statistical processing and analysis of the sample 12 using the calculated results.

The above-described modified examples are different in the method of correcting a phase delay to calculate a corrected phase delay.

Although the fluorescence detection device using intensity-modulated laser light and the fluorescence detection method according to the present invention have been described above in detail, the present invention is not limited to the embodiment described above. It should be understood that various changes and modifications may be made without departing from the scope of the present invention.

DESCRIPTION OF REFERENCE NUMERALS 10 flow cytometer
12 sample
20 signal processing device
22 laser emitting unit
23 laser light source unit
24, 26 light-receiving unit
24b collecting lens
26a lens system
$26b_1$, $26b_2$, $26b_3$ dichroic mirror
$26c_1$, $26c_2$, $26c_3$, $26c_4$ band-pass filter
27a, 27b, 27c, 27d photoelectric converter
28 control/processing unit
30 tube
32 collection vessel
34 laser driver
40 signal generating unit
42 signal processing unit
46, 47, 48 oscillators
52a to 52d processing circuit
54, 66, 68 amplifier
56 variable amplifier
58 power splitter
60, 62, 52e RF mixers
64 90 degrees hybrid phase shifter
70, 72, 52f low-pass filters
74, 76 high-pass filters
80 analyzing device
82 AD conversion board
84 analyzing device main body
86 FFT processing module
88 amplitude calculation module
90 phase calculation module
92 phase delay calculation module
94 compensated-fluorescence intensity calculation module
96 fluorescence relaxation time calculation module
98 mixing processing module

The invention claimed is:

1. A fluorescence detection device using intensity-modulated laser light, which irradiates a measurement object with the laser light, receives fluorescence emitted from the measurement object to obtain a fluorescent signal, and determines fluorescence relaxation time from the fluorescent signal, the fluorescence detection device comprising:

a laser light source unit emitting the intensity-modulated laser light with which the measurement object is to be irradiated;

a light-receiving unit outputting the fluorescent signal of fluorescence emitted from the measurement object irradiated with intensity-modulated laser light;

a signal generating unit generating a modulation signal having a predetermined frequency to modulate an intensity of the laser light emitted from the laser light source unit and generating, separately from the modulation signal, a first reference signal having a frequency different from that of the modulation signal in synchronization with the modulation signal;

a signal processing unit comprising a first mixer that performs first mixing processing to mix the first reference signal and the fluorescent signal outputted from the light-receiving unit by irradiating the measurement object with the laser light whose intensity has been modulated using the modulation signal and a first low-pass filter that performs, on a mixed signal obtained by the first mixing processing, first low-pass filtering using a cut-off frequency lower than a sum frequency of a frequency of the modulation signal and a frequency of the first reference signal but higher than a difference frequency between the frequency of the modulation signal and the frequency of the first reference signal to output a fluorescent signal-based low-frequency signal; and a fluorescence detection unit that converts the fluorescent signal-based low-frequency signal into a digital signal and calculates a phase of the fluorescent signal relative to the modulation signal using a first signal component of the digital signal which corresponds to the difference frequency to determine a fluorescence relaxation time of the fluorescence emitted from the measurement object from the calculated phase.

2. The fluorescence detection device according to claim 1, wherein the signal generating unit comprises a first oscillator that generates a clock signal, a second oscillator that generates the modulation signal in synchronization with the clock signal generated by the first oscillator, and a third oscillator that generates the first reference signal in synchronization with the clock signal.

3. The fluorescence detection device according to claim 1, wherein the fluorescence detection unit mixes a second reference signal, which is a digital signal having the difference frequency as a frequency thereof, and the digitized fluorescent signal-based low-frequency signal to determine the first signal component.

4. The fluorescence detection device according to claim 3, wherein the fluorescence detection unit generates the second reference signal.

5. The fluorescence detection device according to claim 3, wherein the signal processing unit comprises a second mixer that performs second mixing processing to mix the modulation signal and the first reference signal and a second low-pass filter that performs, on a mixed signal obtained by the second mixing processing, second low-pass filtering using a cut-off frequency lower than the sum frequency but higher than the difference frequency to output a sine-wave signal having the difference frequency as the frequency thereof, and the fluorescence detection unit digitizes the sine-wave signal outputted from the second low-pass filter to generate the second reference signal.

6. The fluorescence detection device according to claim 1, wherein the fluorescence detection unit performs FFT (Fast Fourier Transformation) processing on the digitized fluorescent signal-based low-frequency signal to calculate, as the first signal component, a value of a real part and a value of an imaginary part, which are obtained by the FFT processing and correspond to the difference frequency, and calculates the phase from the value of the real part and the value of the imaginary part.

7. The fluorescence detection device according of claim 3, wherein the light-receiving unit comprises, in addition to a light-receiving element that receives the fluorescence, a light-receiving element that receives side-scattered light obtained by irradiating the measurement object with the laser light, and outputs a light-receiving signal obtained by receiving the side-scattered light, the signal processing unit comprises a third mixer that performs third mixing processing to mix the light-receiving signal and the first reference signal and a third low-pass filter that performs, on a mixed signal obtained by the third mixing processing, third low-pass filtering using a cut-off frequency lower than the sum frequency but higher than the difference frequency to output a light-receiving signal-based low-frequency signal, and the fluorescence detection unit determines a phase of a second signal component of the light-receiving signal-based low-frequency signal, which corresponds to the difference frequency, by mixing the light-receiving signal-based low-frequency signal and the second reference signal or by performing FFT processing on the light-receiving signal-based low-frequency signal, corrects the phase of the fluorescent signal based on the phase of the second signal component, and determines a fluorescence relaxation time of fluorescence emitted from a measurement object using the corrected phase.

8. The fluorescence detection device according to claim 3, wherein the signal processing unit comprises:

a second mixer that performs second mixing processing to mix the modulation signal and the first reference signal and a second low-pass filter that performs, on a mixed signal obtained by the second mixing processing, second low-pass filtering using a cut-off frequency lower than the sum frequency but higher than the difference frequency to output a sine-wave signal having the difference frequency as the frequency thereof, and the fluorescence detection unit digitizes the sine-wave signal outputted from the second low-pass filter to generate the second reference signal, corrects the phase of the fluorescent signal by subtracting a phase of the second reference signal from the phase of the fluorescent signal to determine a fluorescence relaxation time of the fluorescence emitted from the measurement object using the corrected phase.

9. The fluorescence detection device according to claim 8, wherein the fluorescence detection unit determines a phase of the second reference signal by performing FFT processing on the second reference signal or by mixing the second reference signal and a separately-generated sine-wave signal having the difference frequency.

10. The fluorescence detection device according to claim 9, wherein when the fluorescence detection unit mixes the second reference signal and the separately-generated sine-wave signal having the difference signal, a sine signal and a cosine signal are each mixed with the second reference signal and a ratio between a value obtained by mixing the sine signal with the second reference signal and a value obtained by mixing the cosine signal with the second reference signal is calculated to determine a phase of the second reference signal.

11. The fluorescence detection device according to claim 8, wherein when the fluorescence relaxation time of the fluorescence emitted from the measurement object is determined, the fluorescence detection unit further corrects the corrected phase of the fluorescent signal using a previously-determined correction amount to determine the fluorescence relaxation time of the fluorescence emitted from the measurement object using the further corrected phase with the correction amount, and wherein the correction amount is determined so that when a fluorochrome that emits fluorescence with a known fluorescence relaxation time is set as a measurement object, a fluorescence relaxation time determined by measuring fluorescence becomes equal to the known fluorescence relaxation time of the fluorochrome.

12. The fluorescence detection device according to claim 1, wherein the light-receiving unit comprises, in addition to a light-receiving element that receives the fluorescence, a light-receiving element that receives side-scattered light obtained by irradiating the measurement object with the laser light to output a light-receiving signal obtained by receiving the side-scattered light, the signal processing unit comprises a third mixer that performs third mixing processing to mix the light-receiving signal and the reference signal and a third low-pass filter that performs, on a mixed signal obtained by the third mixing processing, third low-pass filtering using a cut-off frequency lower than the sum frequency but higher than the difference frequency to output a light-receiving signal-based low-frequency signal having the difference frequency as a frequency thereof, the fluorescence detection unit determines an amplitude of the light-receiving signal-based low-frequency signal, and the fluorescence detection unit sets the determined amplitude as an intensity of the side-scattered light and sets an amplitude determined from the first signal component as fluorescence intensity to output the side-scattered light intensity, the fluorescence intensity, and the fluorescence relaxation time.

13. A fluorescence detection method using intensity-modulated laser light, in which fluorescence emitted from a measurement object irradiated with laser light is received and fluorescence relaxation time is determined from a fluorescent signal obtained by receiving the fluorescence, the method comprising the steps of:

irradiating the measurement object with laser light whose intensity has been modulated by a modulation signal having a predetermined frequency;

receiving fluorescence emitted from the measurement object irradiated with the laser light by a detection means to acquire a fluorescent signal obtained by the detection means;

generating, separately from the modulation signal, a first reference signal having a frequency different from a frequency of the modulation signal and a phase synchronized with that of the modulation signal;

performing first mixing processing to mix the first reference signal and the fluorescent signal obtained by the detection means by irradiating the measurement object with the intensity-modulated laser light and further performing first low-pass filtering using a cut-off frequency lower than a sum frequency of the frequency of the modulation signal and the frequency of the reference signal but higher than a difference frequency between the frequency of the modulation signal and the frequency of the reference signal to generate a fluorescent signal-based low-frequency signal; and converting the generated fluorescent signal-based low-frequency signal into a digital signal and calculating a phase of the fluorescent signal relative to the modulation signal using a first signal component of the digital signal, the first signal component corresponding to the difference frequency, and determining the fluorescence relaxation time of the fluorescence emitted from the measurement object using the calculated phase.

14. The fluorescence detection method according to claim 13, wherein when a digital sine-wave signal having the difference frequency as a frequency thereof is defined as a second reference signal, the first signal component is determined by mixing the second reference signal and the digitized fluorescent signal-based low-frequency signal.

15. The fluorescence detection method according to claim 14, wherein, in addition to the first mixing processing and the first low-pass filtering performed on the fluorescent signal, the second reference signal is generated by:

performing second mixing processing to mix the modulation signal and the first reference signal, performing, on a mixed signal obtained by the second mixing processing, second low-pass filtering using a cut-off frequency lower than the sum frequency but higher than the difference frequency to output a sine-wave signal having the difference frequency as a frequency thereof and, then digitizing the sine-wave signal obtained by the second low-pass filtering.

16. The fluorescence detection method according to claim 13, wherein when the fluorescence is received, side-scattered light obtained by irradiating the measurement object with the laser light is received in addition to the fluorescence, and a light-receiving signal obtained by receiving the side-scattered light is outputted, and wherein third mixing processing is performed to mix the light-receiving signal and the first reference signal and third low-pass filtering using a cut-off frequency lower than the sum frequency but higher than the difference frequency is performed on a mixed signal obtained by the third mixing processing to output a light-receiving signal-based low-frequency signal, and wherein a phase of a second signal component of the light-receiving signal-based low-frequency signal, which corresponds to the difference frequency, is determined by mixing the light-receiving signal-based low-frequency signal and the digital sine-wave signal having the difference frequency as a frequency thereof or by performing FFT processing on the light-receiving signal-based low-frequency signal, and the phase of the fluorescent signal is corrected based on the phase of the second signal component to determine the fluorescence relaxation time of the fluorescence emitted from the measurement object using the corrected phase.

17. The fluorescence detection method according to claim 13, wherein when the fluorescence relaxation time of the fluorescence emitted from the measurement object is determined from the phase of the fluorescent signal, the phase of the fluorescent signal is corrected using a previously-determined correction amount and the fluorescence relaxation time of the fluorescence emitted from the measurement object is determined using the corrected phase, and wherein the correction amount is determined so that when a fluorochrome that emits fluorescence with a known fluorescence relaxation time is set as a measurement object to measure fluorescence, the fluorescence relaxation time determined from the corrected phase becomes equal to the known fluorescence relaxation time of the fluorochrome.

* * * * *